United States Patent [19]

Al-Sioufi

[11] Patent Number: 4,880,602
[45] Date of Patent: * Nov. 14, 1989

[54] METHOD AND DEVICE FOR DISINFECTING BIOLOGICAL FLUIDS AND CONTAINER FOR SAME

[76] Inventor: Habib Al-Sioufi, P.O. Box 654, Brookline, Mass. 02146

[ * ] Notice: The portion of the term of this patent subsequent to Jun. 23, 2004 has been disclaimed.

[21] Appl. No.: 58,553

[22] Filed: Jun. 5, 1987

Related U.S. Application Data

[63] Continuation-in-part of Ser. No. 780,668, Sep. 29, 1989, Pat. No. 4,675,159.

[51] Int. Cl.$^4$ ............................................. A61L 2/18
[52] U.S. Cl. ..................................... 422/28; 422/36; 422/37; 514/635; 514/642; 514/693; 514/694; 514/731
[58] Field of Search ........................... 422/28, 36, 37; 514/635, 642, 693, 694, 731

[56] References Cited

U.S. PATENT DOCUMENTS 4,657,159  6/1987  Al-Sioufi ............................... 422/36

OTHER PUBLICATIONS

Ascenzi, "Important information Concerning the Reuse of Glutaraldehyde-Based Disinfectants and Their Tuberculocidal Activity," Surgikos, Inc. Research Division, Oct. 1974.
"Vacutainer Brand Evacuated Serum Separation Tube," Becton Dickenson Vacutainer Systems Product Information Sheet, Jun. 1981.
Block, Disinfection, Sterilization and Preservation, Lea & Febiger, Philadelphia, 1983, pp. 52, 197–224.
Bond, "Viral Hepatitis B: Safety in the Immunochemistry Laboratory," The Ligand Quarterly 5, 1982, pp. 34–38.
Bond, "Inactivation of AIDS Virus in Clothing,", J Am Med Assoc, 5/03/85, p. 2580.
Bond, "Effects of Chemical Germicides on Hepatitis B Virus Infectivity," Abstracts of the Annual Meeting of the American Society of Microbiology 1982, 3/05–7/82, pp. 233.
Bond "Inactivation of Hepatitis B Virus by Intermediate-to-High Level Disinfectant Chemicals," J Clin Microbio, 18, 1983, pp. 535–538.
Borick, et al., "Alkanized Glutaraldehyde, a New Antimicrobial Agent," J Pharm Sci, 53, 10/64, pp. 1273–1274.

(List continued on next page.)

Primary Examiner—Garry S. Richman
Assistant Examiner—Jill Johnston
Attorney, Agent, or Firm—Gipple & Hale

[57] ABSTRACT

A technique and receptacle for disinfecting biological fluids such as whole blood is described in which the disinfectant is prepositioned in a receptacle for biological fluids utilized for clinical evaluation in an amount which is sufficient to disinfect the fluid without interfering with subsequent clinical evaluation. The invention is specifically directed to disinfecting viral contaminants in blood by providing a closed container for the blood specimen which contains an amount of a disinfectant sufficient to destroy without otherwise affecting the integrity of the specimen for future evaluation. The amount of disinfectant positioned in the container is adjusted to provide an ultimate concentration in the blood specimen of aldehyde of about 0.001 to 5.0 weight percent and is buffered to a pH of about 7.2 to 8.5 percent preferably about 7.4. To increase the stability and shelf life of the sample container and disinfectant, activation or buffering to the indicated pH range does not take place until or just prior to introduction of the specimen into the container. In a particularly preferred embodiment of the invention, the close sample container is evacuated and provided with an elastomeric stopper adapted to receive the hollow needle of a syringe whereby the blood specimen is introduced into the container directly from the donor. The aldehyde based disinfectant used in accordance with the invention have also been found to facilitate separation of the fluid components of the blood by causing gelling of cellular blood components.

22 Claims, 6 Drawing Sheets

OTHER PUBLICATIONS

Crow, "Cleaning, Disinfecting Procedures Help Control Spread of Infection," Hosp J Amer Hosp Assoc, 52, 12/01/78.

Davis, "Sterilization and Disinfection," Microbiology, including Immunology and Molecular Genetics, Philadelphia, 1980, pp. 1268–1274.

Derby, et al., "Clinical Evaluation of Glutaraldehyde-Phenate (Sporcidin) Used to Disinfect Athroscopes," Orthapaedic Nursing 3, 9–10/84.

Derevjanik, et al. "Evaluation of Sporcidin and Cidex Following Clinical In-Use Conditions," J Dent Res 62, Abstracts, 3/83.

Dumon, et al., "Effectiveness of basic glutaraldehyde as a disinfectant in bronchical fiberscopy."

Durheim, et al., "Customer Products Profile," 3M Brand Disinfecting and Sterilizing Solution, St. Paul, Minn.

Favero, "Sterilization, Disinfection and Antisepsis in the Hospital," Manual of Clinical Microbiology, 3rd Ed., 1980, pp. 952–953.

Hagan, "Clinical Observations on Sterilizing Cystoscopes with Glutaraldehyde-Phenate," Urology 23, 2/84.

Johnson, et al., "Two Per Cent Glutaraldehyde: A Disinfectant in Arthroscopy and Arthroscopic Surgery," J Bone & Joint Surgery 64A, 1982, pp. 237–239.

Kalt, "The relationship between cleavage and blastocoel formation in Xenopus laevis," J. Embryol 26, 1971, pp. 51–66.

Kalt, et al., "A Study of Fixation of Early Amphibian Embryos for Electron Microscopy," Ultrastructure Research 36, 1971, pp. 633–645.

Kennedy, "Evaluation of a glutaraldehyde-phenate solution used to disinfect endoscopes and instruments in a freestanding surgical facility," J Operating Room Research Institute 3, 8/83.

Klein, et al., "The Inactivation of Viruses by Germicides," School of Medicine, Temple University, Philadelphia, pp. 116–118.

Leach, "A New Synergizer Glutaraldehyde-Phenate Sterilizing Solution and Concentrated Disinfectant," Infection Control 2, 1981, pp. 3–6.

Leach, "Repeated Insult Patch Testing of Sporcidin Diluted 1:16 With 15 Parts Water," Laboratory Results from Milligan College, 3/09/84.

Lennette, "Sterilization, Disinfection and Antisepsis in the Hospital," Manual of Clinical Microbiology 3rd ed., Washington, DC, 1980, pp. 952–956.

Masferrer, et al. "Comparison of Two Activated Glutaraldehyde Solutions Cidex Solution and Sonacide," Respiratory Care 22, 3/77.

Miner, et al., "Antimicrobial and other properties of a new stabilized alkaline glutaraldehyde disinfectant/sterilizer," Am J Hosp Pharm 34, 4/87, pp. 376–382.

Nickel, "The Anesthetist's Role in Prevention of Nosocomial Infections", J Am Assoc Nurse Anesthetics, 6/70, pp. 209–216.

Prince, "Disinfectant Activity Against Bacteria and Viruses: A Hospital Guide," P&MC Hospitals, 4/83, pp. 55–62.

Prince, "Virucide Assay—E.P.A. Method," Laboratory Report from Gibraltar Biological Laboratories, Inc., 1/28/83.

Saitanu, et al., "Inactivation of Enterovirus by Glutaraldehyde," Applied Microbiology 29, 5/75, pp. 571–574.

Snyder, et al., "Alkaline Glutaraldehyde; an effective disinfectant," Am J Hosp Pharm, 6/65.

Spire, et al., "Inactivation of Lymphadenopathy Associated Virus by Chemical Disinfectants," Lancet, 10/20/84, pp. 899–901.

Sporicidin Company Product Information Sheet, 1982.

Sporicidin Company Product Information Sheet, 10/82, vol. 27, No. 10.

Sporicidin Company Hospital Price Sheet "Sporicidin."

Sporicidin Company Product Information Sheet.

Sporicidin Company Product Information Sheet, 1/1/83, "Sporicidin Cold Sterilizing Solution, Questions and Answers."

Stonehill, et al., "Buffered Glutaraldehyde: a new chemical sterilizing solution," Am J. Hosp Pharm 20, 9/63.

Taylor, et al., "For Effective Thermometer Disinfection," Nursing Outlook 14, 2/66.

Townsend, et al., "An Efficacy Evaluation of a synergized Glutaraldehyde-Phenate Solution in Disinfecting Respiratory Therapy Equipment Contaminated During Patient Use," Infection Control 3, 1982, pp. 240–243.

Venoject Product Direction Sheet, "Blood Collection Products, Directions for Use."

Wallbank, "Capsule-Deficient Cryptococcus Neoformans in AIDS Patients," Lancet, 3/16/85, pp. 642.

3M Company Product Information Sheet, "Glutarex Disinfecting and Sterilizing Solution," 1981.

3M Company Product Information Sheet, "3M Disinfecting and Sterilizing Solution," 1979.

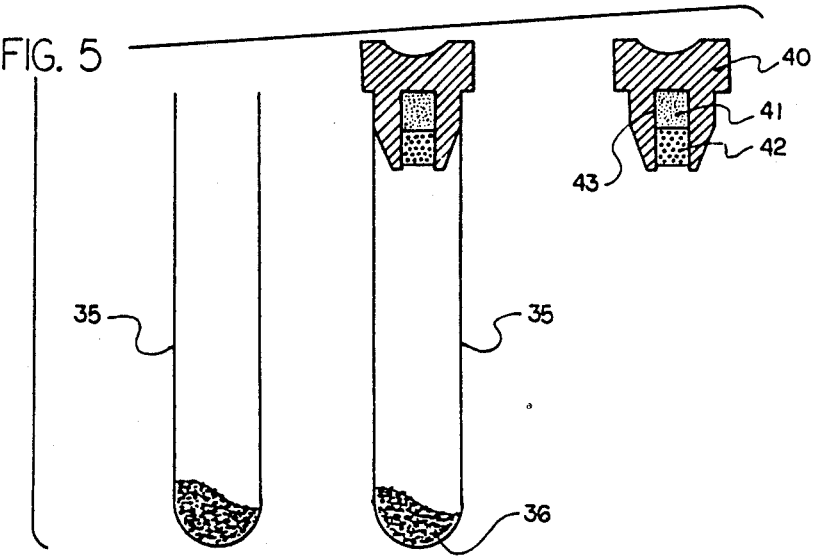
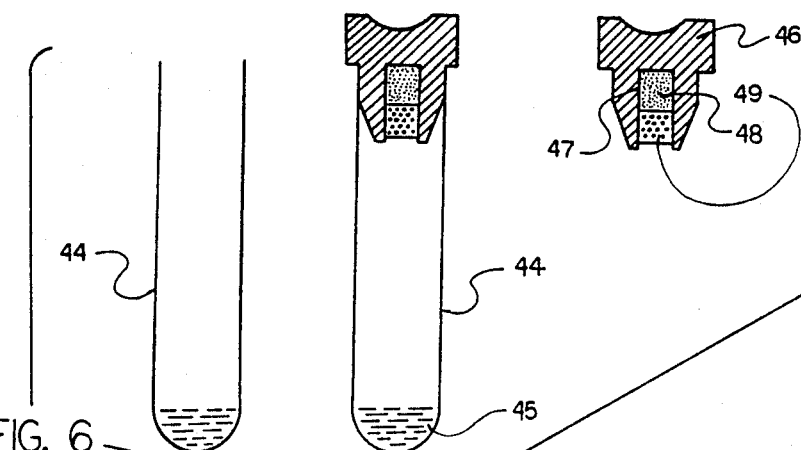

METHOD AND DEVICE FOR DISINFECTING BIOLOGICAL FLUIDS AND CONTAINER FOR SAME

CROSS REFERENCE TO RELATED PATENT APPLICATION

This application is a continuation-in-part of application Ser. No. 780,668 filed Sept. 29, 1985, now U.S. Pat. No. 4,675,159.

SUMMARY OF THE INVENTION

The present invention is directed to a device and method for combating and destroying biological contamination in specimens of biological fluids such as blood intended for medical evaluation without interfering with the integrity of the proposed evaluation. More specifically, the present invention is particularly concerned with disinfecting viral contamination in biological specimens to avoid infecting those coming in contact either with the specimen itself or the receptacles and equipment used to contain and evaluate the specimen. Of particular concern in the present invention is the avoidance of contamination by HTLV-III Virus responsible for Acquired Immune Deficiency Syndrome and Hepatitis Virus which may be present in blood specimens drawn for medical evaluation. Additionally, it has been found that aldehyde based disinfectant compositions used in accordance with the invention as viral disinfectants facilitate separation of the fluid components of the blood by causing gelling and fixing of cellular components.

BACKGROUND OF THE INVENTION

The incidence of hospital acquired infections has been increasing in recent years at an alarming rate which has caused great concern among the staffs of hospitals and especially those working in the laboratories. While many disinfection and sterilization techniques have been employed to alleviate this problem in different functional sections of the hospital, these techniques have not consistently provided a safe environment for the staff. Frequently, the disinfection and sterilization techniques which have been used have been employed after overt contamination has taken place from spilling, broken samples, etc. While these techniques have helped to reduce the incidence of laboratory acquired infections, they have not curtailed them. With the increasing incidence of contagious pathogens that can be transmitted by patient's specimens, especially blood and particularly such dangerous contaminants as the AIDS and hepatitis viruses, a new and safe technique for handling laboratory specimens is needed.

Various disinfectants and sterilizing agents have been employed with varying degrees of success, both in hospitals and other environments, Monoaldehydes such as formaldehyde have been used successfully as a disinfectant, however, dialdehydes, particularly glutaraldehyde, are preferred. Examples of glutaraldehyde-based disinfectants are a dilute sodium phenate-glutaraldehyde solution buffered to pH 7.4, an activated solution which contains 2.0% glutaraldehyde buffered to pH 7.5–8.0 and a disinfectant and sterilizing solution containing 2% glutaraldehyde at pH 7.0–7.5.

The extensive use of glutaraldehyde based compositions as an antiseptic and disinfectant has led to extensive of the compound and its activity. Glutaralde been classified as a chemosterilizer and has been Borick, *J. of Pharm. Sciences*, vol. 53, no. 10, Oct. 1964, as a chemical agent capable of destroying all forms of microbiological life including bacterial fungus spores, tubercle bacilli and viruses. The compound in fact been shown to be effective against a wide range of viruses even in the presence of high levels of organic matter which tend to destroy the potency of other disinfectants. The degree of biocidal activity observed in glutaraldehyde solutions is very much dependent on the pH of the solution as enhanced biocidal activity is found in alkaline solutions.

Boucher et al., *Proc. West Pharmacal Soc.* 16, pp. 282–288, 1973, postulated that the biocidal activity of gluaraldehyde is controlled by the distance between the aldehyde groups and their tendency to polymerize, thereby allowing free aldehyde groups to interact with the amino groups of the bacterial cell. This agrees with the findings of Rubbo et al., *J. Appl. Bacteriol* 30, pp.78–87, 1967, that antibacterial activity is due to the two aldehyde groups present on the molecule. After considering these results, Navarro and Monsan, *Ann. Microbol* 127B, pp.295–307, 1976, concluded that only structures containing two aldehyde groups allow formation of an aldol type polymer at an alkaline pH, and also produces a similar sterilizing effect at acid pHs on increasing concentrations. In other words, while the extent of polymerization is considerable at alkaline pHs, it is negligible in acid solutions unless the concentration is increased. On the other hand, acid solutions at pH3–4 of glutaraldehyde are considerably more stable than alkaline solutions.

The antimicrobal activity in any compound can not be viewed in isolation but must be described with reference to a number of factors including pH, temperature, organic matter present, and concentration. For glutaraldehyde, it has been common to use a 2% solution at room temperature and an alkaline pH of about 7.9. Unfortunately, alkaline solutions of glutaraldehyde are much less stable than acid solutions owning to the polymerization reactions already described, with a corresponding loss of antimicrobiol activity. A reduction in sporicidal activity of activated glutaraldehyde on storage has been observed in reports of Kelsey et al., *J. Clin. Pathol.* 27, pp.632–638, 1974, Thomas and Russell, *J. Appl. Microbiol* 28, pp.331–225, 1974b, Gorman and Scott, *Int. J. Pharma* 4, pp.57–65, 1979a. This reduction in sporicidal activity is directly related to a drop in concentration of the free aldehyde which appears to be essential for biological activity. Borick, *Adv. Appl. Microbiol* 10, pp. 291–312, 1968, has estimated that glutaraldehyde concentration actually falls from 2.1% at pH 8.5 to 1.3% at pH 7.4 over a period of twenty-eight days at ambient temperatures. Accordingly, it has generally been the practice to employ glutaraldehyde as a 2% solution to which an activator is added to bring the pH to approximately 8 at the time of use. Such a solution used at room temperature will, for example, disinfect within 10 minutes and sterilize within 10 hours. However, it has been recommended that this solution be discarded after 14 days because of the significant decrease in activity and free aldehyde concentration. This instability has lead to the development of more stable preparations formulated at lower pHs and some with other potentiators included to increase the otherwise low level of activity observed at lower pH.

The inevitable conditions of clinical use for disinfection and sterilization frequently mean that organic matter is present such as blood and pus. This organic matter can act either by protecting the microbial species from antimicrobial attack or by competing with the microbial cell for active sites on the disinfectant molecules, thus reducing the effective concentration of disinfectant substance. Accordingly, many otherwise effective disinfectants and sterilizing agents may become ineffective where organic material, such as blood, is contacted. Glutaraldehyde, however, has a high resistance to neutralization by organic matter. Borick et al., *J. Pharm. Sci.* 53, pp. 1273-1275, 1964, for example has reported that the presence of 20% blood serum did not appear to adversely effect the activity of glutaraldehyde while Synder and Cheatle, *Am. J. Hosp. Pharm.* 22, pp. 321-327, 1965, have reported that 1% whole blood did not effect glutaraldehyde activity.

One of the most important considerations in selecting a suitable disinfectant, in addition to its potency and sustained effectiveness as a disinfectant, is the toxicity of the composition to individuals coming in contact with it. Various studies have shown that glutaraldehyde, in moderate effective concentrations, is generally only slightly irritating to the skin, mucous membranes and eyes. Sato and Dobson, *Arch. Dermatol* 100, pp. 564-569, 1969, have found that 5% glutaraldehyde was only irritating if the epidermal barrier was not intact.

Aqueous solutions of glutaraldehyde have been used to treat hyperhydrosis and it has been used topically in the treatment of onychomycosis. Prevention of dental calculus formation and reduction of dental cavity formation in the mouth has been achieved by using oral compositions incorporating glutaraldehyde. In the cosmetic field, glutaraldehyde has been proposed for disinfection of production equipment and as a preservative. Glutaraldehyde has been used as a disinfectant for control of mastitis.

Accordingly, glutaraldehyde is now a generally accepted disinfectant and is found in a number of commercial preparations for disinfection and sterilization. Babb et al., *J. Hosp. Infec.* 1, pp. 63-75, 1980, for example, have compared nine glutaraldehyde products.

Glutaraldehyde has also been used extensively in various non-microbiological areas including the leather tanning industry and tissue fixation for electromicroscopy. In microbiological areas, glutaraldehyde has been employed principally as a liquid chemical sterilizing agent for medical and surgical material that cannot be sterilized by heat or irradiation. Compared with other disinfectants, glutaraldehyde has been found to be superior for disinfection of face masks, breathing tubes and other respiratory therapy equipment. Important advantages of glutaraldehyde as a chemosterilizer are: its activity in the presence of organic material, non-corrosive action towards metals, rubber, lenses and most materials, and lack of deleterious effect on cement and lenses of endoscopes. Further, glutaraldehyde has been recommended for decontamination of dental, surgical instruments and working surface where the hepatitis B surface antigen may be present as well as for the treatment of warts.

From the above mentioned studies, testing any biological specimen containing glutaraldehyde will not damage the instrument used in testing. Osterberg, *Arch. Pharm. Chemi. Sci. Ed.* 6, pp. 241-248, 1978, found that damage to leukocytes was apparent only above a 100 microg/ml. glutaraldehyde level. In addition, no erythrocyte damage occurred at the glutaraldehyde concentrations used.

The use of aldehydes in electron microscopy was extensively studied and it was found that many cytochemical reactions can be performed on tissue specimens after aldehyde fixation. Glutaraldehyde is effective in preserving both prokaryotes and eukaryotes, including fragile specimens such as marine invertebrates, embryos, diseased cells and fungi. Glutaraldehyde stabilized blood plasma with little shrinkage of blood clots (Chambers et al. 1968, *Arch. Pathol.* 85,18.). Tissue specimens can be left in this fixative for many hours without apparent deterioration. Presently, glutaraldehyde is the most efficient and reliable fixative for preservation of biological specimens for routine electron microscopy and the previously mentioned and available data indicate that proteins are not denatured to any marked extent by fixation with glutaraldehyde (M. A. Hayat, *Fixation for Electromicroscopy*, Academic Press, 1981). Similarly, glutaraldehyde fixed-erythrocytes remain sensitive to the hemagglutination and hemagglutination inhibition tests for arbovirus antigens and antibodies (Wolff et al. [1977] *J. Clin Microbiol.* 6.55). Differential staining of viable and nonviable cells with alcian blue is maintained after fixation with glutaraldehyde (Yip and Auerperg, 1972, In Vitro 7, 323). From the above mentioned studies, glutaraldehyde will preserve the biological specimens without otherwise affecting the integrity of the specimen for future evaluation.

As set forth above, the handling of biological specimens such as blood after sampling, during storage and medical evaluation poses a particular hazard for those coming in contact with the specimens, especially where there is a possibility of AIDS (HTLV-III) or Hepatitis Virus being present. Despite the known effectiveness of disinfectants such as glutaraldehyde in destroying these viruses, their use has essentially been limited to the containers and equipment coming in contact with the fluid, and only after such contact has occurred and the fluid disposed of. What remains especially hazardous is the contaminated body fluids themselves, such as AIDS (HTLV-III) or Hepatitis infected blood, which are carriers of the infection from the time they are drawn from the donor. Accordingly, what is needed is a technique for destroying such viral contamination instantaneously when the sample is taken, but without effecting the specimens for further testing.

DISCUSSION OF THE PRIOR ART

U.S. Pat. No. 3,016,328 describes disinfecting with a sporicidal composition containing a $C_2$ to $C_6$ saturated dialdehyde, such as glutaraldehyde, and an alkalinating agent in either alchoholic or aqueous solution at a pH above 7.4.

U.S. Pat. No. 3,282,775 describes disinfecting with a sporicidal composition containing a $C_2$ to $C_6$ saturated dialdehyde preferably glutaraldehyde and a cationic surface active agent.

U.S. Pat. No. 3,708,263 describes sterilizing at temperatures below 75° C. by contacting the equipment to be treated with an aqueous solution by pH 2 to 8.5 containing glutaraldehyde and DMSO simultaneously with ultrasonic wave energy.

U.S. Pat. Nos. 3,912,450; 3,968,248; and 3,968,250 describe disinfection or sterilization compositions that contain nonionic and anionic surfactants with aqueous or alchoholic glutaraldehyde solutions.

U.S. Pat. No. 4,093,744 describes sporicidal compositions containing glutaraldehyde at pH 6.5 to 7.4 which may contain a detergent and also a monoaldehyde.

U.S. Pat. No. 3,983,252 describes disinfectant compositions that contain a dialdehyde and an alkaline metal salt of a hydrocarbon carboxilic acid in aqueous solution and optionally an alcohol of up to seven carbon atoms or a diol with up to 4 carbon atoms such as ethylene glycol, propylene glycol, butylene glycol and/or a triol glycerol. The compositions are described as having improved stability in the pH range of 6 to 7.4.

U.S. Pat. No. 4,103,001 describes a sterilizing composition containing glutaraldehyde, a phenol and a metal phenate as active ingredients. The composition may also contain a humectant such as glycerol, propylen glycol or diethylene glycol.

U.S. Pat. No. 4,436,754 describes a disinfectant and sterilizing composition having low odor and irritation potential which is an aqueous solution containing a 2 to 6 carbon atom dialdehyde and may also contain formaldehyde and a diol or mono-substituted diol. Such compositions can be used at pH of 2 to 9.

U.S. Pat. No. 3,886,269 describes a formaldehyde based disinfectant formed by passing formaldehyde gas through a solvent such as dimethyl sulfoxide or dimethyl formamide to form a gel-like polymer. The disinfectant described exhibits disinfection properties against basterial vegetative cells, bacterial spores, and soil organisms.

U.S. Pat. No. 4,048,336 describes the use of a combination of glutaraldehyde and a monoaldehyde such as a formaldehyde to kill spores on instruments.

M. A. Hayat in *Fixation for Electromicroscopy*, Academic Press, 1981, pages 64 to 147 describes fixative agents for preserving and fixing blood and/or tissue specimens.

Seymour S. Block in *Disinfection, Sterilization and Preservation*, Lea and Febiger, 1983, Chapters 2, 3, 9 and 22 describes sterilization techniques using glutaraldehyde and phenolic compounds.

DESCRIPTION OF THE INVENTION

In accordance with the present invention, a disinfectant for viral and other contamination in biological fluids such as blood is provided in a container for the biological fluid in an amount which is effective to destroy the contamination without otherwise compromising the integrity of the fluid specimen with regard to subsequent biomedical evaluation. Additionally, the aldehyde based disinfectant compositions used in connection with the invention facilitate separation of blood components by causing gelling of cellular components. The present invention is particularly adapted for use with evacuated containers into which freshly drawn specimens of blood are introduced and held for subsequent study. Such containers typically consist of a cylindrical tube having one open end into which an elastomeric stopper is fitted which is capable of accepting a hollow syringe needle to permit introduction of the biological fluid into the tube. Vessels of this sort are commercially available under the name of Vacutainer Systems from Becton-Dickinson for example and are evacuated to provide a partial vacuum and provided with a hollow syringe needle which is disposed so that blood is drawn from the donor into the tube by the force of the vacuum in the tube.

According to the invention, the receptacle for receiving and holding the specimen of a biological fluid such as blood is provided with a disinfectant prior to introduction of the biological fluid in an amount sufficient to destroy viral contamination in the fluid and the receptacle without compromising the integrity of the specimen for medical evaluation. The disinfectant can be a mono or dialdehyde such as either glutaraldehyde or formaldehyde or chlorhexidine, phenols or quaternary ammonium compounds or mixtures thereof. The effective concentration of disinfectant according to the invention is about 0.001 to 5.0 weight percent, based upon the total quantity of biological fluid to be placed in the receptacle. Thus, the actual amount of the disinfectant present in the receptacle before introduction of the fluid will depend on the size of the receptacle and the extent to which it is to be filled with fluid since the fluid is, in effect, the principal diluent.

Additional aldehydes such as formaldehyde can also be used in amounts of about 0.001 to 5 percent by weight based on the total biological fluid. Where glutaraldehyde is the disinfectant employed in accordance with the invention, it is desirable to maintain a slightly alkaline pH of preferably about 7.2 to 8.5 preferably 7.4 in order to achieve maximum effect against viral contaminants.

As demonstrated in the prior art, however, glutaraldehyde undergoes increasing polymerization at alkaline pHs and the glutaraldehyde should be maintained at acid pH until just before use. While the receptacle can be provided with an alkalinating agent such as sodium bicarbonate, sodium phenate, or lower alkanols, which is isolated from the disinfectant until just before introducing the biological fluid, it is preferred according to the invention to increase the pH of the glutaraldehyde by introduction of the blood specimen itself which has a normal pH of about 7.4. Where buffering to a higher pH is required, suitable amounts of alkalinating agent can be used.

Typical phenolic based and quaternary ammonium based disinfectants which can be used in the present invention are described in Seymour Block's *Disinfection, Sterilization and Preservation*, 3rd Edition, Lea & Febiger, 1983 at chapters 9 and 14 respectively, which is incorporated herein by reference. Suitable phenolic compounds in addition to carbolic acid are halogen substituted phenols especially with the halogen being in the ortho or para position relative to the nuclear hydroxyl group. Also preferred are halogen substituted phenols having aliphatic or aromatic substituents on the benzene nucleus, such as ortho alkyl derivative of p-chlorphenol and o-chlorophenol and para and ortho bromophenols.

Suitable quaternary ammonium compounds for the present invention include polysubstituted quaternary ammonium salts such as alkyldimethyl benzene ammonium saccharinate, and alkyldimethylethylbenzyl ammonium cyclohexysulfamate, Bis-quaternary ammonium salts such as 1,10-bis(2methyl-4-aminoquinolinium chloride)-decane, polymeric quaternary ammonium salts such as poly[oxyethylene(dimethylimino) ethylene(dimethylimino)-ethylene dichloride], poly[N-[3(dimethylammonio)propyl]-N'-[3-(ethylenoxyethylene-dimethylammonio)propyl] urea dichloride], and $\alpha$4-[1-tris(2hydroxyethyl) ammonium chloride-2-butenyl]poly[1-demethyl ammonium chloride-2-butenyl]-$\omega$-tris(2-hydroxyethyl) ammonium chloride. Also useful are twin chain quaternary alkyl benzyl ammonium chlorides such as octyl decyl dimethyl ammonium chloride, dioctyl dimethyl ammonium chloride, didecyl dimethyl ammonium chloride and dual quaternary-n-alkyl dimethyl ethyl ammonium chloride and n-alkyl dimethyl ethyl ammonium chloride.

It is also desirable to incorporate into the receptacle of the present invention effective amounts of substances to increase the permeability of the cell membrane to allow the disinfectant to reach intracellular pathogens more quickly. Such substances are dimethyl sulfoxide, and glycerol, either alone or in combination. Additionally, other substances whose use in connection with sampling and testing of biological fluids, such as blood, can be used such as anticoagulants, preservatives and biocidal agents. By employing the various configurations which are embodiments of the present invention, activation of the disinfectant can take place prior to, during or after introduction of the specimen and the disinfectant can be released either before, during or after the specimen is introduced. The present invention will however be more fully appreciated by having reference to the drawings.

The use of aldehyde based disinfectants such as glutaraldehyde in accordance with the invention has also been found to facilitate separation of fluid components of the blood by acting as a fixative and causing gelling of the cellular blood components to occur. The following is an example of this separation procedure.

A 10 ml blood sample was drawn and divided into nine 1 ml aliquots. A 25% glutaraldehyde solution was added to each of these aliquots in the following amounts: 25, 50, 75, 100, 125, 150, 175, 200 and 250 microliters. No separation of blood components was observed in the aliquots containing 75 or more microliters of glutaraldehyde, however, in the samples containing 25 and 50 microliters the red blood cell components formed a gel that remained separate from the clear plasma component.

BRIEF DESCRIPTION OF THE DRAWINGS

FIG. 5 illustrates an embodiment of the present invention also similar to that of FIGS. 1 and 4 in which the stopper contains activator and disinfectant separated;

FIG. 6 illustrates an embodiment similar to that of FIG. 5 having an anticoagulant rather than an inert barrier material;

DETAILED DESCRIPTION OF THE DRAWINGS

Figure 1:
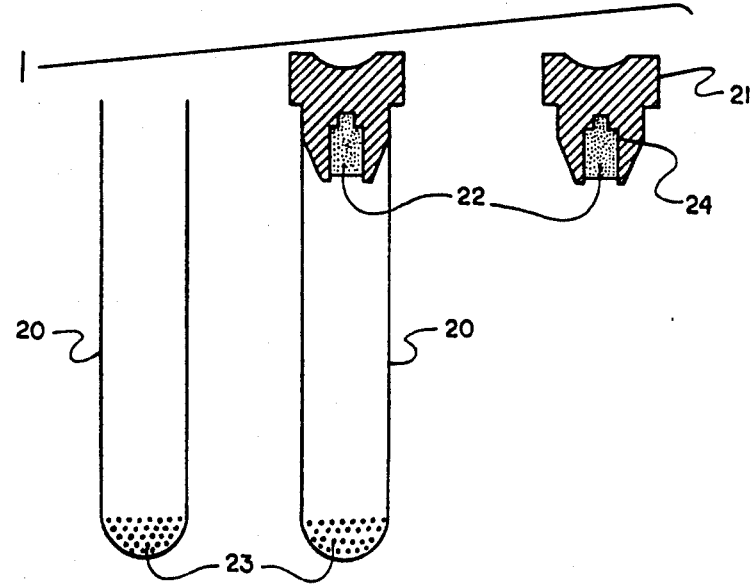
FIG. 1 illustrates one embodiment of the invention in which a closed tube is used having a stopper in one end and containing a disinfectant and activator.

Directing attention to the drawings, FIG. 1 illustrates an embodiment of the present invention in which a cylindrical tube 20 closed at one end is provided with an elastomeric stopper 21 at the other end. As previously noted, closed stopper tubes of similar construction are commonly employed for collecting samples of blood. It is frequently the case that these tubes are provided with a partial vacuum and a double ended hollow syringe needle placed in the stopper end so that the blood sample can be drawn directly from the donor into the tube using the vacuum in the tube. Although the details of construction of these syringe devices is not herein illustrated since they are well known in the art, it will be understood that they can be used in connection with the present invention. In accordance with the embodiment of the invention shown in FIG. 1, a disinfectant material 23 is redisposed in the bottom of the tube 20 and a suitable alkaline activator 22 such as sodium bicarbonate is provided in a cavity 24 of the stopper 21. The two materials are thus kept separate from one anther until the blood sample is introduced through the stopper into the tube whereby the mixing of the disinfectant and activator takes place. It will be understood that the amount of disinfectant present in the bottom of the tube 20 will depend upon the size of the tube and the quantity of blood to be drawn into the tube and should be sufficient to insure a concentration of between 0.001 and 5.0 disinfectant once the blood sample is in the tube. The amount of activator present in the stopper cavity 24 will be sufficient to insure that the specimen and disinfectant have an alkaline pH between 7.2 and 8, preferably about 7.4.

Figure 2:
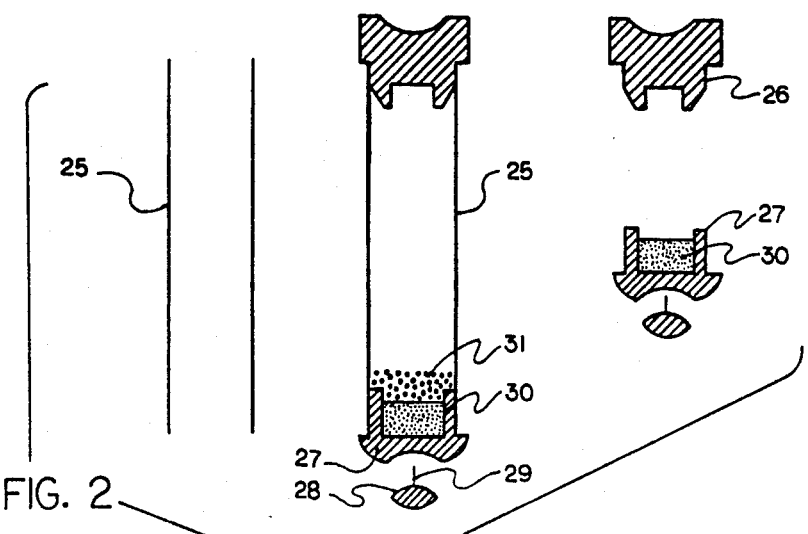
FIG. 2 illustrates an additional embodiment of the present invention whereby both ends of the tube are stoppered and one stopper is provided with the disinfectant or activator

In the embodiment of the invention shown in FIG. 2, the cylindrical tube 25 is provided with a stopper at either end. The lower end of the tube 25 is closed by elastomeric stopper 27 having a recess which contains an activator such as sodium bicarbonate 30 which is separated by thin membrane from the disinfectant 31 which is disposed freely in the tube. The other end of the tube is closed by stopper 26. A sharp pin 29 having a head 28 is provided for piercing the membrane separating the activator and disinfectant before or once the blood sample has been introduced into the other end of the tube 25 through stopper 26.

Figure 3:
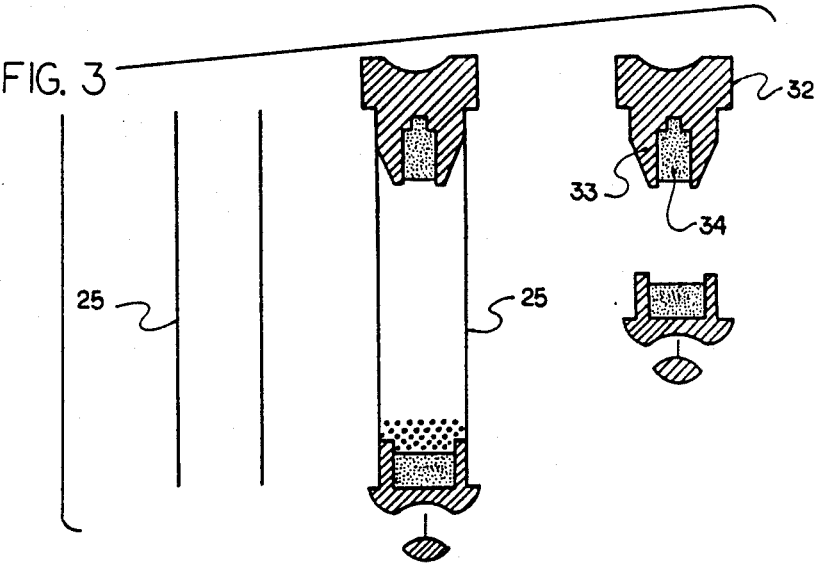
FIG. 3 illustrates an embodiment of the present invention similar to that of FIG. 2 in which one stopper contains anticoagulant.

FIG. 3 of the drawings illustrate an embodiment of the invention similar to that of FIG. 2 except that the upper end of the tube 25 is provided with a stopper 32 having a recessed area 33 provided with an anticoagulant 34 separated from the disinfectant to maintain the fluidity of the blood sample. Introduction of the blood sample through the stopper 32 releases the anticoagulant by rupturing a barrier to allow it to mix with the blood sample, disinfectant and activator which are released by the means of a pin.

Figure 4:
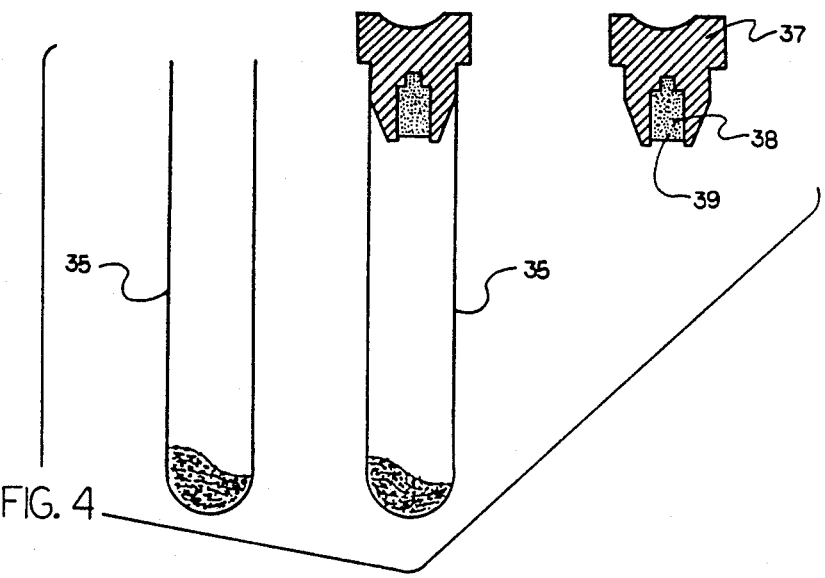
FIG. 4 illustrates an embodiment of the present invention similar to that of FIG. 2 except for the presence of an inert barrier material.

In FIG. 4 of the drawings, an embodiment of the invention otherwise similar to that of FIG. 1 is illustrated in which an activator 39 is provided in the cavity 38 of stopper 37 in the top of the tube. The disinfectant is however mixed with an inert barrier material and placed at the bottom of the tube 36. In this manner, activation of the disinfectant to the appropriate pH will not occur until the blood sample is centrifuged to produce a separation of the serum.

In FIG. 5 of the drawings, the stopper 40 is provided with a recess 43 containing the activator 41 and disinfectant material 42 which are separated from one another by a thin membrane and from the inside of the tube. Inert barrier material is provided at the bottom of the tube 36.

The embodiment of the invention as shown in FIG. 6 is similar to that of FIG. 5 except that the inert barrier material is replaced with an anticoagulant 45.

Figure 7:
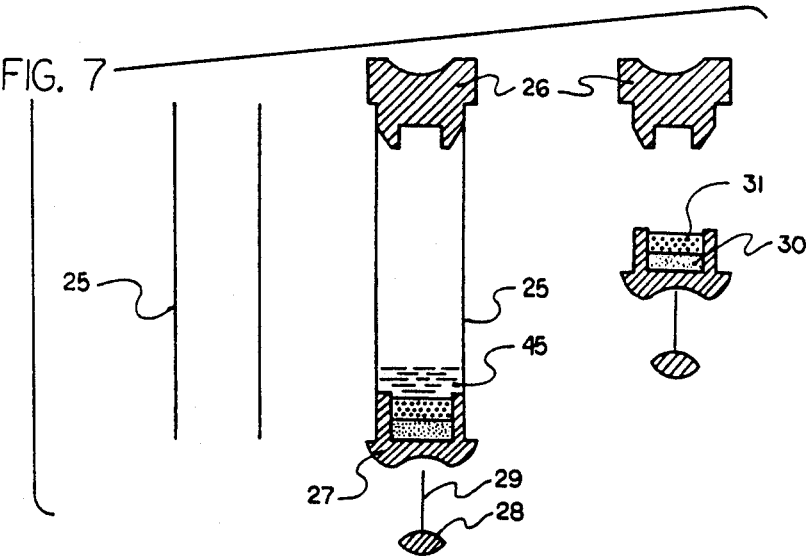
FIG. 7 illustrates an embodiment of the present invention having a tube similar to that of FIG. 2 in which one stopper contains activator and disinfectant separated from each other and containing anticoagulant.

FIG. 7 of the drawings illustrates an additional embodiment of the invention whereby stoppers are provided at both ends of the tube 25. The stopper 27 closing the lower end of the tube is provided with an activator at 30 and disinfectant 31 separated from one another by a thin membrane and from the inside of the tube. Anticoagulant 45 is placed in the tube directly over the stopper and disinfectant material. A pin 29 with head 28 is available to puncture the separating membranes to permit the materials to mix with the blood introduced through stopper 26 at the other end of the tube.

Figure 8:
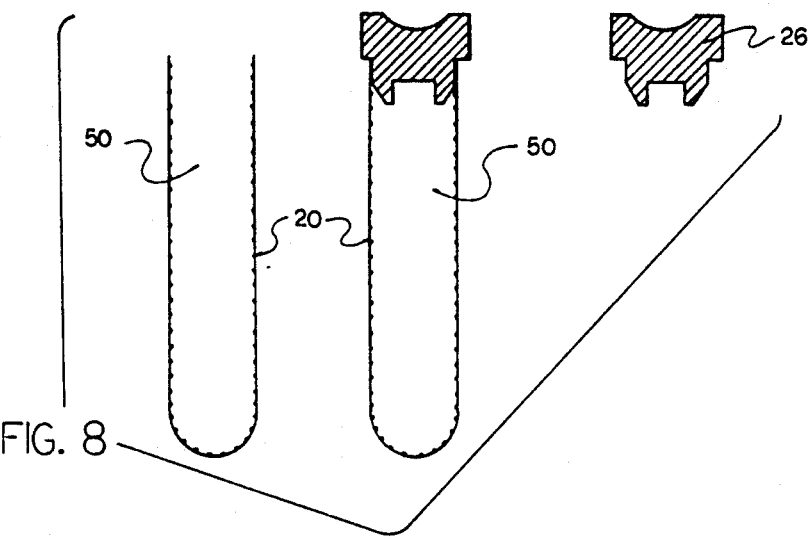
FIG. 8 illustrates an embodiment of the present invention having a tube similar to that of FIG. 1 but containing a disinfectant on the walls of the tube without activator.

FIG. 8 of the drawings illustrates a preferred embodiment of the invention in which disinfectant material 50 is coated on the inside of the tube 20 to provide a layer. The upper end of the stop of the tube 20 is closed by stopper 26 but no additional activator is provided since the amount of disinfectant 50 is adjusted so that its pH will become slightly alkaline with the introduction of blood into the tube which also provides the necessary dilution to result in a concentration of 0.001 to 5% disinfectant.

Figure 9:
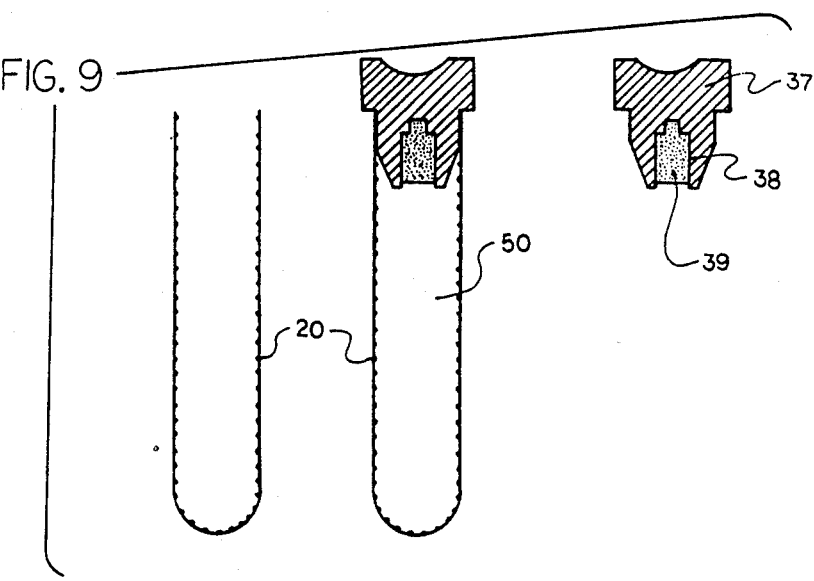
FIG. 9 illustrates an embodiment of the present invention similar to that of FIG. 8 except that activator is contained in the stopper.

In FIG. 9 of the drawings, an embodiment of the invention is shown similar to that of FIG. 8 in that the disinfectant material is a coating 50 on the inside of the tube 20. An activator such as sodium bicarbonate is provided and separated from the inside of the tube, however, in cavity 38 of stopper 37 at 39.

Figure 10:
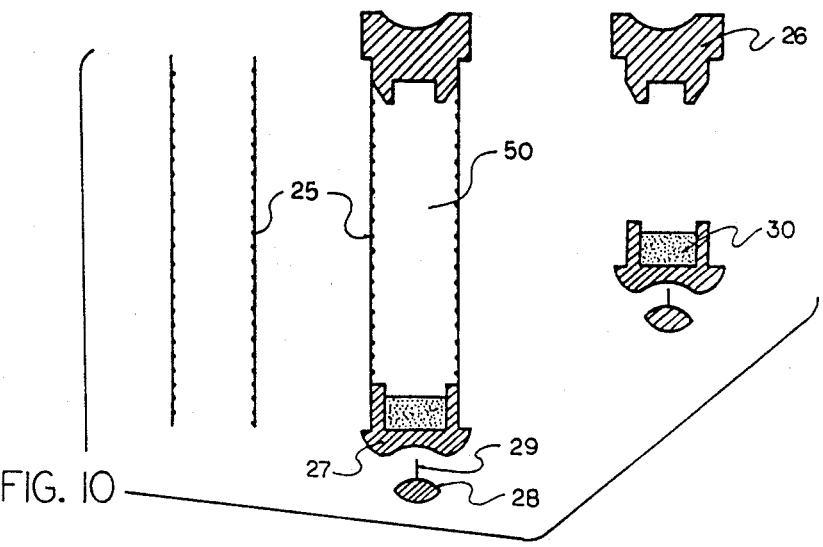
FIG. 10 illustrates an embodiment of the present invention similar to that of FIG. 2 but with disinfectant on the inner walls of the tube.

FIG. 10 of the drawings illustrates the embodiment of the invention whereby the cylindrical tube 25 is closed at both ends by respective stoppers 26 and 27. The stopper 27 is however provided with activator 30 which is separated from the inside of the tube and released into the tube to interact with the disinfectant 50 by inserting the pin 29 into the stopper 27 to rupture a membrane that separates the activator from the interior of the tube.

Figure 11:
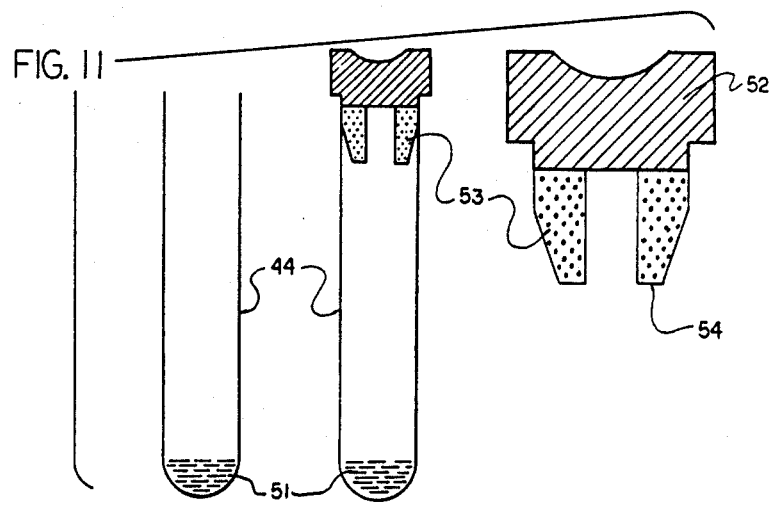
FIG. 11 illustrates an embodiment of the present invention in which a stopper is used which contains disinfectant and having a permeable membrane.
Figure 12:
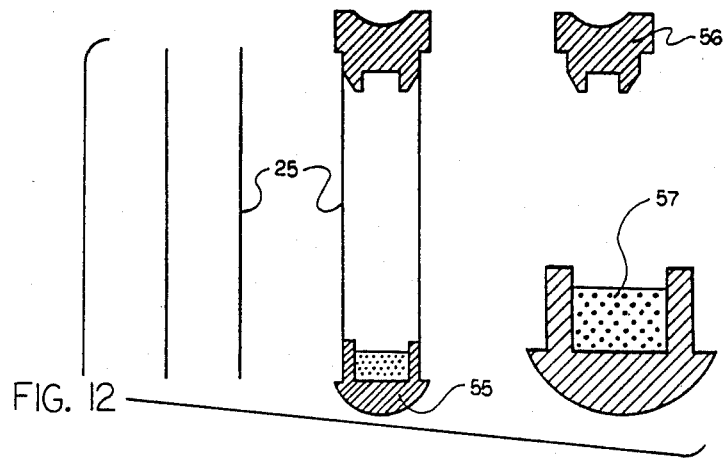
FIG. 12 illustrates an embodiment of the invention similar to that of FIG. 2 except that no activator is used in connection with the disinfectant and a stopper is used having a permeable membrane.

In FIG. 11 of the invention, either an anticoagulant or activator 51 is provided in the bottom of the tube 44. A porous material container 54 is provided on stopper 52 to hold the disinfectant 53 and permit it to diffuse through a permeable membrane into the tube 44 once the fluid specimen has been introduced into the tube and the tube inverted. In FIG. 12 of the drawings, the disinfectant material 57 is provided in an appropriate cavity in stopper 55 closing one end of the tube while stopper 56 closes the other end of the tube. A membrane prevents the disinfectant from entering the tube itself until blood is introduced, at which time the disinfectant diffuses through the membrane into the specimen.

It will be understood that while various preferred embodiments of the present invention have been described herein in order to illustrate and disclose Applicant's invention, additional variations and applications of the present invention are considered to fall within the scope thereof.

What is claimed:

1. A biological fluid disinfecting device comprising an evacuated receptacle for holding a specimen of biological fluid for clinical evaluation which is closed at one of its ends by an elastomeric stopper adapted to be penetrated by means for introducing said specimen therein, said receptacle also containing prior to introduction of said specimen about 0.001 to 5.0 weight percent based on the total fluid of a disinfectant for viral infection present in the specimen which disinfectant is one or more compounds or mixtures thereof selected from the group consisting of glutaraldehyde, formaldehyde, chlorohexidine, phenols and guaternary ammonium compounds.

2. The receptacle of claim 1 which also contains an activator for said disinfectant.

3. The receptacle of claim 1 wherein both ends of said receptacle are closed by elastomeric stoppers.

4. The receptacle of claim 3 wherein both of said stoppers are provided with cavities adapted to retain material until said biological fluid is introduced into said receptacle, the stopper adapted for penetration by said means for introducing the fluid being also adapted to release said material retained therein on penetration, and the other of said stoppers being provided with separate means to release material contained therein into said receptacle.

5. The receptacle of claim 4 wherein the material retained in one of the said stoppers is disinfectant.

6. The receptacle of claim 5 wherein said disinfectant is glutaraldehyde and said biological fluid is blood, said glutaraldehyde being present in an amount such that introduction of said blood dilutes its concentration to about 0.001 to 5.0 weight percent based on the combined blood and glutaraldehyde.

7. The receptacle of claim 5 wherein an alkaline buffering agent is also retained in one of said stoppers in an amount sufficient to adjust the pH of the biological fluid in said receptacle to about 7.2 to 8.5.

8. The receptacle of claim 5 wherein an alkaline buffering agent is disposed therein separate from said disinfectant prior to introducing said blood therein in an amount sufficient to accomplish buffering of the blood and disinfectant to a pH of 7.2 to 8.5.

9. The receptacle of claim 1 wherein said disinfectant is disposed in the end of said receptacle remote from said stopper.

10. The receptacle of claim 1 wherein said biological fluid is whole blood.

11. The receptacle of claim 10 wherein the concentration of said disinfectant is about 0.13 to 2.0 weight percent.

12. The receptacle of claim 10 which also contains an effective amount of anticoagulant for said blood.

13. The receptacle of claim 10 which also includes an effective amount of a substance or substances to enhance cell permeability selected from the group consisting of dimethyl sulfoxide and glycerol.

14. The receptacle of claim 1 wherein an alkaline buffering agent disposed therein is separated from said glutaraldehyde prior to introducing said biological fluid, in an amount sufficient to accomplish buffering to a pH of about 7.2 to 8.5 when said fluid is introduced into the receptacle.

15. The receptacle of claim 14 wherein said buffering agent is selected from the group consisting of sodium bicarbonate, sodium phenate and alkanols of 2–4 carbons.

16. The receptacle of claim 1 wherein said disinfectant is buffered to a pH of about 7.4 by of a said biological fluid and said fluid is blood.

17. The receptacle of claim 1 wherein said disinfectant is glutaraldehyde at acid pH.

18. The receptacle of claim 17 wherein either said disinfectant or said buffering agent is disposed in a cavity in said stopper such that introduction of biological fluid through said stopper causes said disinfectant or agent to be released into said receptacle and whichever of the agent or disinfectant is not disposed in said stopper is otherwise present in said receptacle.

19. The receptacle of claim 1 wherein said disinfectant is coated onto the inside wall thereof.

20. The receptacle of claim 1 in which said receptacle is evacuated to provide a partial vacuum in the interior thereof.

21. A method for destroying viral contamination in specimens of biological fluids which comprises providing an evacuated container for said fluids having predisposed therein about 0.001 to 5.0 weight percent of a disinfectant for said viral contamination selected from the group consisting of glutaraldehyde, formaldehyde, chlorhexidine, phenols and quaternary ammonium compounds or mixtures thereof, said disinfectant being buffered substantially at the time said biological fluid is introduced therein to a pH of about 7.2 to 8.5.

22. An evacuated receptacle for receiving and retaining a specimen of blood for clinical evaluation, comprising a closed, elongated cylinder having an elastomeric stopper closing at least one of its ends and adapted to receive and be penetrated by means for introducing said blood specimen into said cylinder; the interior of said cylinder being provided prior to introducing said blood specimen with a disinfectant for viral contamination and preservation of said specimen selected from the group consisting of glutaraldehyde, formaldehyde, chlorhexidine, phenols and quaternary ammonium compounds or mixtures thereof, in an amount sufficient for said disinfection but insufficient to clinical evaluation of said specimen, the amount of said disinfectant being further sufficient to insure a concentration of about 0.001 to 5.0 weight percent based on the combined sample and disinfectant and a pH of about 7.2 to 8.5

* * * * *